US011730669B2

(12) United States Patent
Lee

(10) Patent No.: US 11,730,669 B2
(45) Date of Patent: Aug. 22, 2023

(54) HIGH FREQUENCY CHEST WALL OSCILLATOR

(71) Applicant: KONINKLIJKE PHILIPS N.V., Eindhoven (NL)

(72) Inventor: Seunghyun Lee, Valrico, FL (US)

(73) Assignee: Koninklijke Philips N.V., Eindhoven (NL)

(*) Notice: Subject to any disclaimer, the term of this patent is extended or adjusted under 35 U.S.C. 154(b) by 267 days.

(21) Appl. No.: 16/294,051

(22) Filed: Mar. 6, 2019

(65) Prior Publication Data

US 2019/0274919 A1    Sep. 12, 2019

Related U.S. Application Data

(60) Provisional application No. 62/638,999, filed on Mar. 6, 2018.

(51) Int. Cl.
*A61H 23/00* (2006.01)
*A61B 7/00* (2006.01)
*A61B 7/04* (2006.01)
*A61H 31/00* (2006.01)

(52) U.S. Cl.
CPC .............. *A61H 31/00* (2013.01); *A61B 7/003* (2013.01); *A61B 7/04* (2013.01); *A61H 23/006* (2013.01);
(Continued)

(58) Field of Classification Search
CPC .................. A61H 31/00; A61H 23/006; A61H 2201/165; A61H 2201/5058;
(Continued)

(56) References Cited

U.S. PATENT DOCUMENTS 6,139,505 A * 10/2000 Murphy ................. A61B 5/061
381/67
6,443,907 B1 * 9/2002 Mansy .................... A61B 7/04
600/529
(Continued)

FOREIGN PATENT DOCUMENTS

EP        2520268 A1    11/2012
WO    WO2017194713 A1    11/2017

OTHER PUBLICATIONS

PCT International Search Report, International application No. PCT/EP2019/055083, dated May 29, 2019.

*Primary Examiner* — Timothy A Stanis
*Assistant Examiner* — Kelsey E Baller
(74) *Attorney, Agent, or Firm* — Daniel H. Brean; Andrew M. Gabriel

(57) ABSTRACT

The present disclosure pertains to a system configured to determine one or more parameters of chest wall oscillation therapy for a subject. The system includes a wearable garment configured to provide percussion to one or more parts of a lung of a subject. The wearable garment includes: percussion excitation elements configured to produce the percussion; and sensors configured to generate output signals conveying information related to a response of the one or more parts of the lung to the percussion. The system includes a control unit configured to determine frequency and energy density information for the sounds made by the one or more parts of the lungs caused by the percussion, the frequency and energy density information determined based on the output signals; and determine the one or more parameters of the chest wall oscillation therapy based on the frequency and energy density information.

20 Claims, 4 Drawing Sheets

(52) U.S. Cl.
CPC ............... *A61H 2201/165* (2013.01); *A61H 2201/5043* (2013.01); *A61H 2201/5058* (2013.01); *A61H 2205/084* (2013.01)

(58) Field of Classification Search
CPC .... A61H 2201/5007; A61H 2201/5023; A61H 2201/1619; A61H 2201/5097; A61H 2201/1207; A61H 2201/1238; A61H 23/004; A61H 23/04; A61H 23/02; A61H 2230/40; A61H 2205/084; A61H 2023/002–045; A61H 9/0007; A61B 7/003; A61B 7/04; G01N 2800/382
See application file for complete search history.

(56) References Cited

U.S. PATENT DOCUMENTS

| | | | |
|---|---|---|---|
| 8,038,633 B2* | 10/2011 | Van Brunt | A61H 9/0078 601/152 |
| 8,734,370 B1* | 5/2014 | Ignagni | A61H 23/0263 601/152 |
| 9,943,461 B1* | 4/2018 | Muench | A61H 31/006 |
| 9,956,134 B2* | 5/2018 | Shockley, Jr. | A61H 23/0254 |
| 10,292,890 B2* | 5/2019 | DeVliegar | A61H 23/006 |
| 2012/0157857 A1* | 6/2012 | Abe | A61B 7/003 600/484 |
| 2013/0267877 A1 | 10/2013 | Van Brunt | |
| 2014/0276271 A1* | 9/2014 | Stryker | A61H 23/04 601/46 |
| 2017/0007494 A1 | 1/2017 | Rock | |
| 2017/0027813 A1* | 2/2017 | Bobey | A61H 9/0078 |
| 2017/0100304 A1* | 4/2017 | Venkataraya | A61M 15/0021 |
| 2017/0112707 A1 | 4/2017 | Huster | |
| 2017/0281460 A1 | 10/2017 | Zgoda | |
| 2018/0132815 A1* | 5/2018 | Tsai | A61B 5/0004 |
| 2018/0177483 A1* | 6/2018 | Ye | A61B 5/0015 |
| 2020/0100981 A1* | 4/2020 | Bobey | A61H 7/004 |

* cited by examiner

HIGH FREQUENCY CHEST WALL OSCILLATOR

CROSS-REFERENCE TO RELATED APPLICATIONS

This patent application claims the priority benefit under 35 U.S.C. § 371 of International Patent Application No. PCT/EP2019/055083 filed Mar. 1, 2019, which claims the priority benefit under 35 U.S.C. § 119(e) of U.S. Provisional Application No. 62/638,999, filed on Mar. 6, 2018, the contents of which are herein incorporated by reference.

BACKGROUND OF THE INVENTION

1. Field of the Invention

The present disclosure pertains to a system and method for determining one or more parameters of chest wall oscillation therapy for a subject.

2. Description of the Related Art

Administration of high frequency chest wall oscillations (HFCWO) therapy is typically subjective and based on the clinician's skills and years of experience to accurately assess the patients. Some clinicians simply prescribe one set of therapy settings (frequency and intensity) for all their patients. Some clinicians prescribe a protocol that can sweep the entire range of frequency settings from low to mid to high frequency setting at fixed amount of duration (e.g., 2 min each frequency setting), hoping that one of those settings would yield the most optimum therapy for the patient. The present disclosure overcomes at least these deficiencies in prior art systems.

SUMMARY OF THE INVENTION

Accordingly, one or more aspects of the present disclosure relate to a system configured to determine one or more parameters of chest wall oscillation therapy for a subject. The system comprises a wearable garment configured to provide percussion to one or more parts of a lung of a subject. The wearable garment comprises (i) one or more percussion excitation elements configured to produce the percussion, the percussion comprising mechanical pulsation of a chest wall of the subject in proximity to the one or more parts of the lung; and (ii) one or more sensors configured to generate output signals conveying information related to a response of the one or more parts of the lung of the subject to the percussion, the response comprising sounds made by one or more parts of the lungs caused by the percussion. The system comprises a control unit operatively coupled to the one or more percussion excitation elements and the one or more sensors configured to (a) cause the one or more percussion excitation elements to produce the mechanical pulsation (b) determine frequency and energy density information for the sounds made by the one or more parts of the lungs caused by the percussion, where the frequency and energy density information is determined based on the output signals, and (c) determine the one or more parameters of the chest wall oscillation therapy based on the frequency and energy density information.

Another aspect of the present disclosure relates to a method for determining one or more parameters of chest wall oscillation therapy for a subject with a system comprising a wearable garment configured to provide percussion to one or more parts of a lung of a subject and a control unit. The method comprises producing, with one or more percussion excitation elements in the wearable garment the percussion, the percussion comprising mechanical pulsation of a chest wall of the subject in proximity to the one or more parts of the lung; generating, with one or more sensors in the wearable garment, output signals conveying information related to a response of the one or more parts of the lung of the subject to the percussion, the response comprising sounds made by one or more parts of the lungs caused by the percussion; determining, with the control unit, frequency and energy density information for the sounds made by the one or more parts of the lungs caused by the percussion, the frequency and energy density information determined based on the output signals; and determining, with the control unit, the one or more parameters of the chest wall oscillation therapy based on the frequency and energy density information.

Still another aspect of the present disclosure relates to a system configured for determining one or more parameters of chest wall oscillation therapy for a subject. The system comprises means for providing percussion to one or more parts of a lung of a subject. The means for providing percussion comprises (i) means for producing the percussion, the percussion comprising mechanical pulsation of a chest wall of the subject in proximity to the one or more parts of the lung; and (ii) means for generating output signals conveying information related to a response of the one or more parts of the lung of the subject to the percussion, the response comprising sounds made by one or more parts of the lungs caused by the percussion. The system comprises means for determining frequency and energy density information for the sounds made by the one or more parts of the lungs caused by the percussion, the frequency and energy density information determined based on the output signals; and means for determining the one or more parameters of the chest wall oscillation therapy based on the frequency and energy density information.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
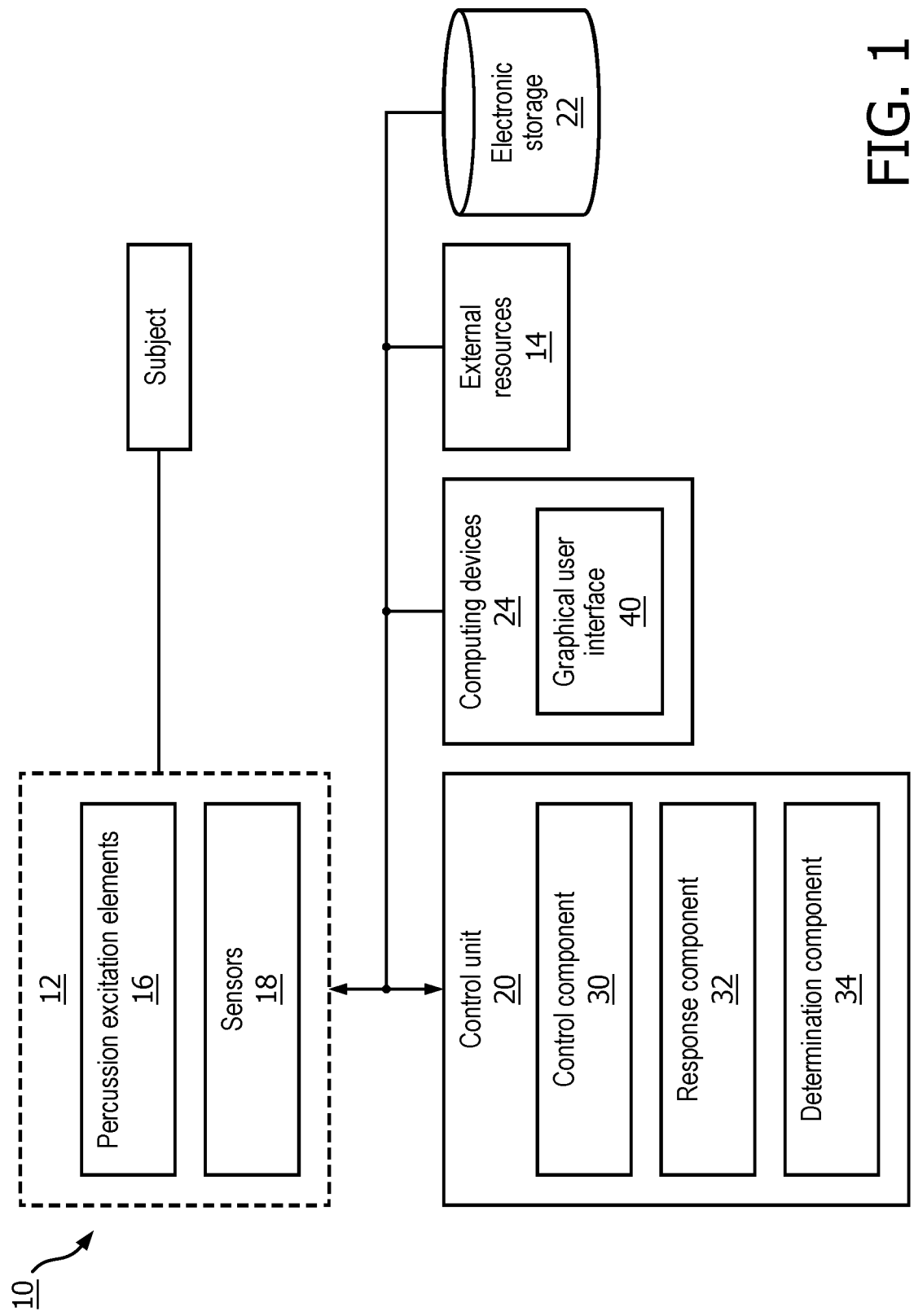
FIG. 1 is a schematic illustration of a system configured to determine one or more parameters of chest wall oscillation therapy for a subject, in accordance with one or more embodiments.

As used herein, the singular form of "a," "an," and "the" include plural references unless the context clearly dictates otherwise. As used herein, the term "or" means "and/or" unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic illustration of a system 10 configured to determine one or more parameters of chest wall oscillation therapy for a subject, in accordance with one or more embodiments. Percussion plays a role as a basic clinical assessment tool, when performed in conjunction with other techniques such as auscultation, palpation, and imaging. Clinical percussion is generally described as tapping (e.g., previously with either a percussion hammer or fingers, for example) to determine the area under the perused is whether air filled, fluid filled, or solid. This information allows for a better understanding of the underlying disease processes. Percussion may be a valuable tool to assess the secretion clearance need for patients with chronic secretion retention problem and requiring daily airway clearance therapy (e.g., cystic fibrosis and bronchiectasis patients).

Currently, the main choice of the airway clearance therapy for these groups of patients is High Frequency Chest Wall Oscillation (HFCWO). HFCWO devices may be configured to deliver pulsating air percussion therapy to patient's chest with frequency and intensity settings that applies to the entire lung. The frequency may be typically set from 5 Hz to 20 Hz, and the intensity is usually adjusted using a 1 to 10 scale. The intensity level is typically adjusted based on patient's comfort and tolerance. However, what is ideal frequency setting for each patient is less clear and poorly understood.

Generally, a successful administration of HFCWO therapy is still subjective and based on the clinician's skill and years of experience to accurately assess patients. Many clinicians simply prescribe one set of therapy setting (frequency and intensity) for all their patients, or they prescribe a protocol that can sweep the entire range of frequency setting from low to mid to high frequency setting at fixed amount of duration (e.g., 2 min each frequency setting), hoping that one of those settings would yield the most optimum therapy for the patient.

System 10 of the present invention optimizes airway clearance therapy (e.g., HFCWO therapy) using percussion sound analysis, by identifying the optimum therapy settings for specific areas of the lungs. System 10 is configured such that the specific resonant frequency response from diagnostic percussion may reveal the ideal natural frequency setting to maximize the vibration of the airway thus optimizing the mobilization of the retained secretion in the airway. System 10 facilitates a diagnostic percussion method that provides "tap and listen" approach on multiple locations on the lung. Each area of the percussed lung field may provide different resonance response, thus different optimum frequencies for different areas of the lung may be provided. This approach allows a more targeted frequency setting for each area of the lung (e.g., each lobe of lung), which allows for a more effective therapy.

In some embodiments, a diagnostic percussion system 10 may be integrated (or used in conjunction with) an airway clearance system. For example, the integration may be in the form of a wearable device or garment. Such a combination system, capable of delivering diagnostic percussion and optimizing the therapy setting for each area of the lung based on the percussion sound analysis, may significantly improve the overall efficacy of airway clearance therapy in patients.

In some embodiments, system 10 comprises one or more of percussion excitation element(s) 16, sensor(s) 18, control unit 20, electronic storage 22, client computing device(s) 24, external resources 14, and/or other components. In FIG. 1, percussion excitation element(s) 16, sensor(s) 18, control unit 20, electronic storage 22, external resources 14, and client computing device(s) 24 are shown as separate entities. In some embodiments, some or all of the components of system 10 and/or other components may be grouped into one or more singular devices (e.g., a wearable device, wearable garment, a medical device, or other user devices).

In some embodiments, a wearable device may include a housing, one or more sensors (e.g., sensor(s) 18), processors (e.g., control unit 20), percussion excitation elements (e.g., percussion excitation element(s) 16), or other components. In some embodiments, the wearable device may be any device that is worn, or that is in full or partial contact with any body parts of the subject. In some embodiments, the wearable device may be configured to include one or more sensors, one or more control units, and one or more percussion excitation elements within the housing. In some embodiments, the wearable device may be configured to include one or more sensors, and one or more percussion excitation elements within the housing and one or more control units outside of the housing. In some embodiments, the wearable device may be configured to include one or more control units and one or more percussion excitation elements within the housing and one or more sensors outside of the housing. Such sensors, control units, percussion excitation elements, and other components of the wearable device, whether housed within or outside of the housing, may communicate with one another via wired or wireless connections. It should be noted that, although some embodiments are described herein with respect to a wearable device performing certain operations, one or more such operations may be performed by one or more other components (e.g., one or more servers, client devices, etc.). As an example, such other components (e.g., one or more servers, client devices, etc.) may include one or more processor components that are the same as or similar to components 30-34 described below.

Percussion excitation element(s) 16 is configured to produce clinical percussion. In some embodiments, the clinical percussion comprises mechanical pulsation of a chest wall of the subject. For example, the percussion excitation elements may include one or more drums, cylinders, or other mechanical elements configured to provide mechanical pulsations of the chest wall of the subject. In some embodiments, percussion excitation element(s) 16 may be configured to tap on the chest wall proximate to one or more parts of the subject lungs. In some embodiments, percussion provided by the percussion excitation elements, may produce one or more percussion sounds. Percussion sounds may indicate presence of air, liquid, or solid in the airways of the subject. For example, percussion excitation element(s) 16 may produce resonant, hyper-resonant, stony dull, and/or dull sounds. In general, a more dull sound indicates the presence of a solid mass in the airway and a resonant sound indicates the absence of a solid mass. For example, different amounts of mucus accumulation in the airway can be identified with different percussion sound profiles. An air-trapped airway due to a complete mucus plug can be described as hyper-resonant sound when percussed. The mucus plug or complete blockage of airway due to a localized consolidation may provide dull sound. A partially occluded airway due to mucus yields a specific resonant sound based on the air cavity.

Operations of the percussion excitation elements may be actuated mechanically, electrically, magnetically, thermally, and/or pneumatically. For example, in some embodiments, system 10 may include one or more actuators configured to control percussion excitation element(s) 16 to produce percussion. In some embodiments, the one or more actuators may include mechanical, electrical, and/or magnetic actuators. In some embodiments, the one or more actuators may include hydraulic actuators configured to use hydraulic power to move the percussion excitation elements. In some embodiments, the one or more actuators may include pneumatic actuators configured to use compressed air to control the percussion excitation elements.

In some embodiments, one or more parameters of the clinical percussion produced by percussion excitation element(s) 16 may be adjusted. For example, type of percussion, time interval between the mechanical pulsations, intensity of the pulsations, frequency, and/or other parameters of the percussion may be adjusted by input from users, subjects, one or more component within or outside of system 10. In some embodiments, adjustments to one or more parameters (e.g., type of percussion, time interval, intensity, frequency, etc.) of the clinical percussion may be based on information from individual subjects, information from individual users (e.g., healthcare professionals, caregivers, etc.), manufacturer settings, and/or other information. For example, one or more parameters of the clinical percussion may be adjusted between upper and lower thresholds. The upper and lower thresholds for the parameters may be determined for each subject based on previous diagnosis (or may be based on similarities between subjects). For example, setting the upper and lower thresholds for a given subject may be based on the subject health condition, tolerance, level of comfort, etc. In some embodiments, the parameters of the clinical percussion (e.g., upper and lower thresholds) may be set based on response of one or more other subjects to the clinical percussion. The one or more subjects may have one or more similarities with the subject (e.g., demographic information, vital sign information, medical/health condition information, treatment history information, similar desired outcome, and/or other similarities.

Sensor(s) 18 is configured to generate output signals conveying information related to a response of one or more parts of the lung of the subject to the percussion. In some embodiments, the response includes sounds made by one or more parts of the lungs caused by the percussion. In some embodiments, the one or more sensors are configured to convert sound into an electrical signal. In some embodiments, Sensor(s) 18 may include one or more microphones placed proximate to the percussion excitation elements and configured to detect the sounds caused by the percussion. For example, the one or more microphones may include Micro-Electrical-Mechanical System (MEMS) microphones. In some embodiments, the one or more microphones may include piezoelectric, dynamic, condenser, optical, fiber optic, and/or other types of microphones. In some embodiments, sounds produced by the one or more parts of the lungs of the subject may be output via in an unadulterated format directly to the clinician via a sound output port to support the clinical decision.

Sensor(s) 18 may comprise one or more sensors that generate output signals conveying vital sign and/or physiological information related to the subject. For example, one or more sensor(s) 18 may include a heart rate sensor, a respiration sensor, a movement sensor, a blood pressure sensor, etc. In some embodiments, the sensors generate the one or more output signals continuously and independently of the operations of the other components of system 10. Although sensor(s) 18 is illustrated at a single location near the subject, this is not intended to be limiting. Sensor(s) 18 may include sensors disposed in a plurality of locations, such as for example, coupled (in a removable manner) with clothing of the subject, worn by the subject (e.g., as a part of an object worn by the subject), directly coupled to a body part of the subject (e.g., taped, glued, etc.), positioned to point at the subject while the subject (e.g., a camera, a microphone, etc.), and/or in other locations.

Figure 2:
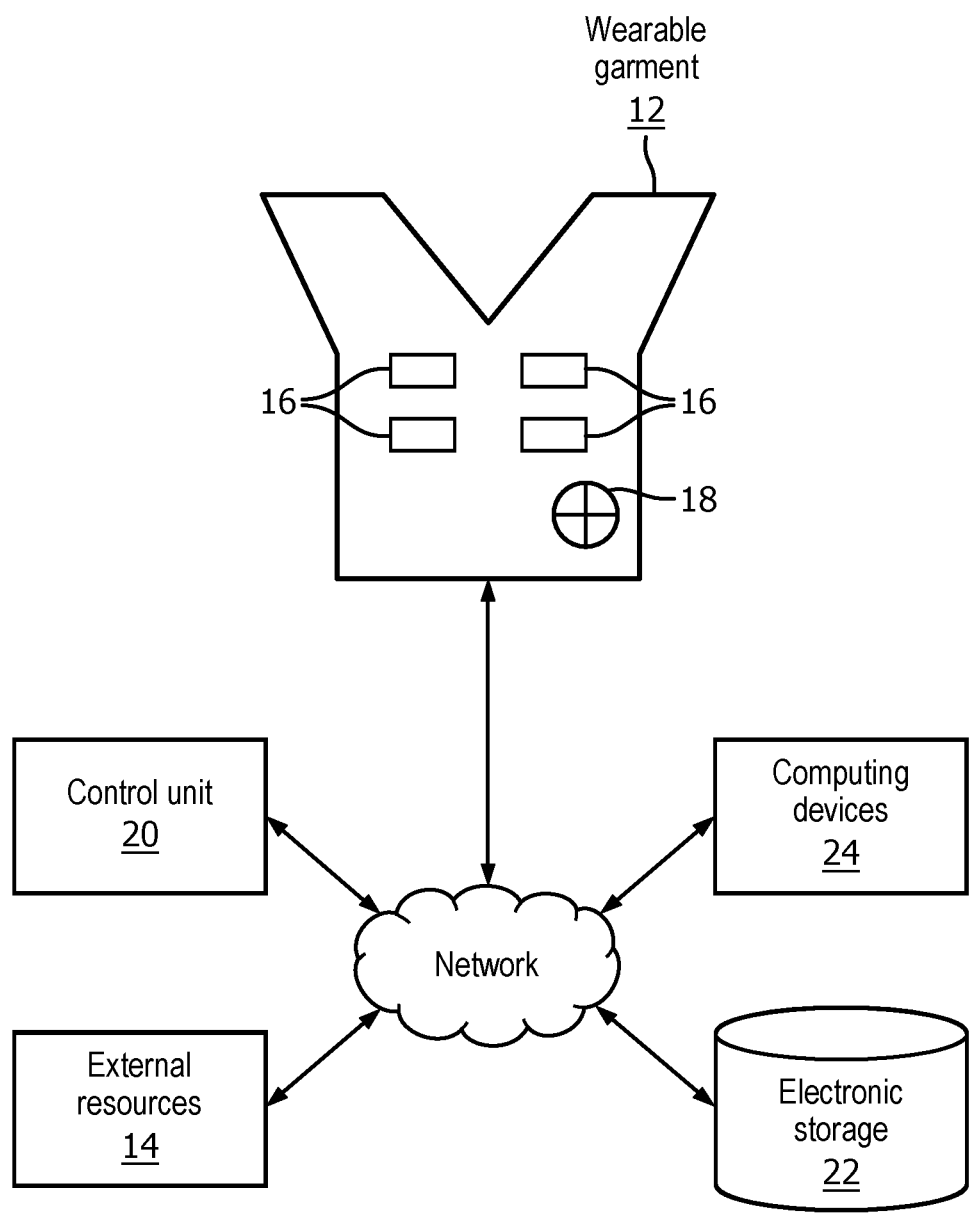
FIG. 2 illustrates example of a system configured to determine one or more parameters of chest wall oscillation therapy for a subject, in accordance with one or more embodiments.

In some embodiments, percussion excitation element(s) 16 and sensor(s) 18 may be part of a wearable garment 12. FIG. 2 illustrates an example of system 10 configured to determine one or more parameters of chest wall oscillation therapy for the subject, in accordance with one or more embodiments. In these embodiments, wearable garment 12 includes percussion excitation element(s) 16 and sensor(s) 18. In some embodiments, other components of system 10 may be included in wearable garment 12 (e.g., control unit 20, electronic storage 22, external resources 14, and client computing device(s) 24, and/or other components). In some embodiments, wearable garment 12 may include any garment or a portion of a garment that is in contact or partial contact with any body part of the subject. In some embodiments, wearable garment 12 may include a clothing, a portion of a clothing, a vest, a shirt, a cloth, a cover, a strap, a band, a tube, etc. In some embodiments, wearable garment 12 may be worn under an airway clearance device (e.g., an HFCWO vest). In some embodiments, wearable garment 12 may be integral (or partially integral) with an airway clearance device.

Control unit 20 is configured to control operations of one or more components of system 10. In some embodiments, control unit 20 may include one or more processors configured to provide information processing capabilities in system 10. As such, control unit 20 may include one or more of a digital processor, an analog processor, and a digital circuit designed to process information, an analog circuit designed to process information, a state machine, and/or other mechanisms for electronically processing information. Although control unit 20 is shown in FIG. 1 as a single entity, this is for illustrative purposes only. In some embodiments, control unit 20 may include a plurality of processing units. These processing units may be physically located within the same device (e.g., a server), or control unit 20 may represent processing functionality of a plurality of devices operating in coordination (e.g., one or more servers, one or more computing devices 24 associated with users, a medical device, wearable garment 12, percussion excitation element(s) 16, sensor(s) 18, a piece of a hospital equipment, devices that are part of external resources 14, electronic storage 22, and/or other devices.)

As shown in FIG. 1, control unit 20 is configured to execute one or more computer program components. The one or more computer program components may comprise a control component 30, a response component 32, a determination component 34, and/or other components. Control unit 20 may be configured to execute components 30, 32, 34, and/or other components by software; hardware; firmware; some combination of software, hardware, and/or firmware; and/or other mechanisms for configuring processing capabilities on control unit 20.

It should be appreciated that although components 30, 32, and 34, are illustrated in FIG. 1 as being co-located within a single processing unit, in embodiments in which control unit 20 comprises multiple processing units, one or more of components 30, 32, 34, and/or other components may be located remotely from the other components. The description of the functionality provided by the different components 30, 32, 34, and/or other components described below is for illustrative purposes, and is not intended to be limiting, as any of components 30, 32, and/or 34 may provide more or less functionality than is described. For example, one or more of components 30, 32, and/or 34 may be eliminated, and some or all of its functionality may be provided by other components 30, 32, and/or 34. As another example, control unit 20 may be configured to execute one or more additional components that may perform some or all of the functionality attributed below to one of components 30, 32, and/or 34.

Control component 30 may be configured to control one or more components of system 10. In some embodiments, control component 30 may be configured to control percussion excitation element(s) 16. In some embodiments, control component 30 may be configured to start, pause, and/or stop the clinical percussion. In some embodiments, control component 30 may control percussion excitation element(s) 16 based on a user selection (e.g., via user interface 24, and/one or more buttons). In some embodiments, control component 30 may control percussion excitation element(s) 16 based on output signals received from sensor(s) 18. For example, in some embodiments, control component 30 may pause or stop the clinical percussion in response to receiving vital sign or physiological information form sensor (s) 18 that indicate that the subject is experiencing difficulties (e.g., difficulty breathing, low heart rate, etc.) In some embodiment, control component 30 may be configured to resume operations of the percussion excitation elements in response to receiving vital sign or physiological information form sensor (s) 18 that indicate that the subject is in a stable condition (e.g., normal vital signs).

In some embodiments, control component 30 may be configured to adjust one or more parameters of clinical percussion. For example, type of percussion, time interval between the mechanical pulsations, intensity of the pulsations, frequency, and/or other parameters of the percussion. In some embodiments, control component may be configured to adjust the one or more parameters of the clinical percussion based on input from users, subjects, and/or one or more component within or outside of system 10. In some embodiments, adjustments to one or more parameters (e.g., type of percussion, time interval, intensity, frequency, etc.) of the clinical percussion may be based on information from individual subjects, information from individual users (e.g., healthcare professionals, caregivers, etc.), manufacturer settings, and/or other information. For example, one or more parameters of the clinical percussion may be adjusted between upper and lower thresholds. The upper thresholds and a lower thresholds may be determined based on the subject, and/or based on other parameters determined by a user (e.g., healthcare professional, caregiver, etc.), and/or one or more components within or outside of system 10.

Response component 32 is configured to receive output signals form sensor 18 indicating a response of one or more parts of the lungs of the subject to the clinical percussion. In some embodiments, the response includes sounds and/or electrical signals representative of sounds made by the one or more parts of the lungs of the subject. In some embodiments, response component 32 may be configured to process the received response before determining one or more parameters of the response. For example, in some embodiments, response component 32 may be configured to receive sound from sensor(s) 18 in the form of a raw sound waveform, convert the sound waveform into a digital signal format (e.g., by passing it through a signal conditioning unit), reduce ambient noise, filter the signal, and/or convert the signal into frequency spectrum. In some embodiments, response component 32 may be configured to determine one or more parameters of the response. In some embodiments, the one or more parameters of the response (e.g., sound) may include frequency and corresponding energy density information for the sounds made by the one or more parts of the lungs caused by the percussion. In some embodiments, response component 32 may be configured to determine the peak resonant frequency of each one of the one or more parts of the lungs. In some embodiments, response component 32 may be configured to output unadulterated percussion sound directly to a user (e.g., a clinician) via a sound output port to support the user's decision. In some embodiment, response component 32 may be configured to output visual information including sound parameters (e.g., frequency and energy density) via user interface 40 (described below). In some embodiments, the output may be in the form of a graphical, digital, textual, and/or other representation format of the sound parameters.

Figure 3:
FIG. 3 illustrates example of one or more parameters of chest wall oscillation therapy for a subject, in accordance with one or more embodiments.

In some embodiments, response component 32 may be configured to record the sound made by the one or more parts of the lungs of the subject (e.g., in the response component 32, storage 22, external resources 14, and/or in other components within or outside system 10). In some embodiments, response component 32 may be configured to record the received sound for a predetermined period of time (e.g., around 0.5 s). In some embodiments, response component 32 may be configured to continuously record the sound received. In some embodiments, response component 32 may be configured to periodically record the received sound. In some embodiments, the sound may be recorded in the raw waveform format. In some embodiments, the sound may be recorded in a processed or partially processed format. In some embodiments, response component 32 may be configured to record the sound (and/or one or more parameters of the sound) along with the one or more parts of the lungs that produced the sound (e.g., anterior upper right lobe, anterior upper left lobe, anterior lower right lobe, anterior lower right lobe, posterior upper right lobe, posterior upper left lobe, posterior lower right lobe, posterior lower right lobe, etc.). FIG. 3 shows an example of one or more parts of the lung (location in the lung values 220) along with corresponding peak resonant frequency values 230. For example, the anterior upper right lobe of the lung of the subject has a peak resonant frequency of 133 Hz.

Determination component 34 is configured to determine one or more parameters of therapy to be delivered to the subject based on the response of the one or more parts of the lung of the subject to the percussion. In some embodiments, the one or more therapy parameters may include one or more of frequency, intensity, duration, time interval between therapies, etc. For example, determination component 34 may be configured to determine parameters of therapy based on the frequency and corresponding energy density information of the sound signals received from one or more parts of the lungs. For example, time to frequency domain transformation such as Fourier transformation and spectrum analysis may be applied to determine the frequency and the energy contents of the percussion sounds. In some embodiments, a low pass filter may be deployed to eliminate other physiologic artifact such as heart beats or other artifacts. For example, a band pass filter between 20 Hz and 400 Hz may be deployed to improve the signal quality. Other active noise cancellation techniques may be used to eliminate possible ambient noise. In some embodiments, the peak resonant frequency of the percussion sound may be used to determine an optimum frequency setting for the therapy. In general, typical resonant frequency range of the lung is between about 20 Hz and about 400 Hz. In some embodiments, the optimum frequency setting for the therapy may be based on secondary frequency components with lower energy density.

In some embodiments, the therapy may include airway clearance therapy, and/or chest wall oscillation therapy (e.g., HFCWO). Generally, HFCWO therapy is used to treat patients with chronic secretion retention problems and who require daily airway clearance therapy, (e.g., cystic fibrosis and bronchiectasis patients). HFCWO devices may be set to deliver pulsating air percussion therapy to patient's chest with different frequency and intensity settings for different areas of the lung. The frequency can be set from 5 Hz to 20 Hz, and the intensity can be adjusted from a 1 to 10 scale. In some embodiments, the peak resonant frequency for each area of the lung (of the percussion sound) may be used to determine an optimum frequency setting for HFCWO devices (for each area of the lung). Each area of the percussed lung may provide different resonance response. Different optimum frequencies for different areas of the lung may be determined. This approach allows a more targeted frequency setting for each area of the lung (e.g., each lobe of lung), which allows for a more effective therapy.

In some embodiments, lower natural frequency setting between 5 Hz and 25 Hz can be selected to achieve harmonics frequency response in the higher frequency range where the lung typically resonate. For example, the peak resonant frequency response from anterior side of the upper right lobe is recorded at 133 Hz. 19 Hz square wave percussion vibration may yield 133 Hz resonance at the 7th harmonics frequency. FIG. 3 shows an example of peak resonant frequency percussion shows an example of one or more parts of the lung (location in the lung values 220) along with corresponding peak resonant frequency values 230, corresponding HFCWO frequency settings 240, and the type of waveform 250.

In some embodiments, system 10 may be used as a diagnostic device configured to detect areas in the lungs that are filled with air, fluid, and/or solids. System 10 can be further configured to determine amount of mucus accumulation in the airway of the subject. In some embodiments, system 10 may be configured to determine optimum settings for a therapy device to be used on the subject based on the detected areas of the lungs (e.g., filled with fluid and/or mucus), based on the amount of accumulations in the subject airways (e.g., mucus accumulation). In some embodiments, system 10 may be used in conjunction with a therapy device. For example, system 10 may be worn under a chest wall oscillation therapy device. In some embodiments, system 10 may be integral with a therapy device (e.g., a chest wall oscillation therapy device). In some embodiments, the therapy device may include a High Frequency Chest Wall Oscillation (HFCWO) device. For example, a wearable HFCWO garment.

In some embodiments, system 10 may include one or more components configured to obtain (and/or determine) subject-specific information. This may improve performance of system 10 and/or the therapy device by using a personalized diagnostic tool (system 10) and a personalized therapy device (personalized settings of the device). In some embodiments, information related to the subject may be determined based on output signals from sensor(s) 18. In some embodiments, information related to the subject may include biographical information. For example, biographical information may include demographic information (e.g., gender, ethnicity, age, etc.), vital sign information (e.g., heart rate, temperature, respiration rate, weight, BMI, etc.), medical/health condition information (e.g., a disease type, severity of the disease, stage of the disease, categorization of the disease, symptoms, behaviors, readmission, relapse, etc.), treatment history information (e.g., type of treatments, length of treatment, current and past medications, etc.), and/or other information.

In some embodiments, system 10 may include one or more components configured to obtain (and/or determine) information related to other subjects. For example, subjects with similar diagnostic information, demographic information, vital sign information, medical/health condition information, treatment history information, treatment goal information, and/or other similarities with the subject. It should be noted that the subject information described above is not intended to be limiting. A large number of information related to subjects may exist and may be used with system 10 in accordance with some embodiments. For example, users may choose to customize system 10 and include any type of subject data they deem relevant. In some embodiments, subject information (related to the subject and/or related to other subjects) may obtained/extracted from one or more databases (e.g., included in electronic storage 22, external resources 14, one or more medical devices, other internal or external databases, and/or other sources of information.

In some embodiments, determination component 34 may be configured to determine operations settings for system 10 (e.g., parameters of percussion delivery) and/or optimum settings for therapy devices based on information from the subject and from subjects having one or more similarities with the subject (e.g., similar diagnostic information, demographic information, vital sign information, medical/health condition information, treatment history information, therapy goal, and/or other similarities with the subject).

In some embodiments, determination component 34 may include one or more models configured to determine operations settings of system 10 and/or a therapy device based on historical data (e.g., subject information from the subject or other subjects). The models may include one or more neural networks (e.g., deep neural networks, artificial neural networks, or other neural networks), other machine learning models, or other models. In some embodiments, the one or models (e.g., a deep neural network or other machine-learning model) may use structured and/or unstructured data for learning. In some embodiments, data may include data received from sensor(s) 18. For example, raw sound, graphical signals, one or more of images, symbols, video, audio, text, and/or other structured data. In some embodiments, learning can be supervised or unsupervised.

External resources 14 include sources of patient and/or other information. In some embodiments, external resources 14 include sources of patient and/or other information, such as databases, websites, etc., external entities participating with system 10 (e.g., a medical records system of a healthcare provider that stores medical history information for populations of patients), one or more servers outside of system 10, a network (e.g., the internet), electronic storage, equipment related to Wi-Fi technology, equipment related to Bluetooth® technology, data entry devices, sensors, scanners, and/or other resources. In some embodiments, some or all of the functionality attributed herein to external resources 14 may be provided by resources included in system 10. External resources 14 may be configured to communicate with control unit 20, computing devices 24, electronic storage 22, and/or other components of system 10 via wired and/or wireless connections, via a network (e.g., a local area network and/or the internet), via cellular technology, via Wi-Fi technology, and/or via other resources.

Electronic storage 22 includes electronic storage media that electronically stores information. The electronic storage media of electronic storage 22 may include one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may be (in whole or in part) a separate component within system 10, or electronic storage 22 may be provided (in whole or in part) integrally with one or more other components of system 10 (e.g., computing devices 24, control unit 20, etc.). In some embodiments, electronic storage 22 may be located in a server together with control unit 20, in a server that is part of external resources 14, in a computing device 24, and/or in other locations. Electronic storage 22 may include one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 22 may store software algorithms, information determined by control unit 20, information received via a computing device 24 and/or graphical user interface 40 and/or other external computing systems, information received from external resources 14, percussion excitation element(s) 16, sensor(s) 18, and/or other information that enables system 10 to function as described herein.

Computing devices 24 are configured to provide interfaces between caregivers (e.g., doctors, nurses, friends, family members, etc.), patients, and/or other users, and system 10. This enables data, cues, results, instructions, recommendations, and/or any other communicable items, collectively referred to as "information," to be communicated between a user (e.g., the subject, a doctor, a caregiver, and/or other users) and one or more of percussion excitation element(s) 16, control unit 20, electronic storage 22, and/or other components of system 10. For example, client computing device(s) 24 may display a representation of the output signal from sensor(s) 18 (e.g., raw sound signals, graphical signals, digital signals, numeric data, video, audio, text, etc.) to a user. In some embodiments, client computing device(s) 24 comprises at least one interface that is provided integrally with control unit 20, percussion excitation element(s) 16, sensor(s) 18, and/or other components of system 10. In some embodiments, individual computing devices 24 may be included, in desktop computers, laptop computers, tablet computers, smartphones, and/or other computing devices associated with individual caregivers, patients, and/or other users. In some embodiments, individual computing devices 24 are, and/or are included, in equipment used in hospitals, doctor's offices, and/or other medical facilities to patients; test equipment; equipment for treating patients; data entry equipment; and/or other devices.

Computing devices 24 are configured to provide information to, and/or receive information from, the caregivers, patients, and/or other users. In some embodiments, computing devices 24 may be configured to output unadulterated percussion sound directly to a user (e.g., a clinician) via a sound output port to support the user's decision. In some embodiments, computing devices 24 are configured to present a graphical user interface 40 to the caregivers to facilitate display representations of the data analysis, and/or other information. For example, computing devices 24 may be configured to output visual information including sound parameters (e.g., frequency and energy density) via user interface 40. In some embodiments, the output may be in the form of a graphical, digital, textual, and/or other representation format of the sound parameters. In some embodiments, graphical user interface 40 includes a plurality of separate interfaces associated with computing devices 24, control unit 20 and/or other components of system 10; multiple views and/or fields configured to convey information to and/or receive information from caregivers, patients, and/or other users; and/or other interfaces.

In some embodiments, computing devices 24 are configured to provide graphical user interface 40, processing capabilities, databases, and/or electronic storage to system 10. As such, computing devices 24 may include control units 20, electronic storage 22, external resources 14, and/or other components of system 10. In some embodiments, computing devices 24 are connected to a network (e.g., the internet). In some embodiments, computing devices 24 do not include control units 20, electronic storage 22, external resources 14, and/or other components of system 10, but instead communicate with these components via the network. The connection to the network may be wireless or wired. For example, control unit 20 may be located in a remote server and may wirelessly cause display of graphical user interface 40 to the caregivers on computing devices 24.

As described above, in some embodiments, an individual computing device 24 is a laptop, a personal computer, a smartphone, a tablet computer, and/or other computing devices. Examples of interface devices suitable for inclusion in an individual computing device 24 include a touch screen, a keypad, touch-sensitive and/or physical buttons, switches, a keyboard, knobs, levers, a display, speakers, a microphone, an indicator light, an audible alarm, a printer, and/or other interface devices. The present disclosure also contemplates that an individual computing device 18 includes a removable storage interface. In this example, information may be loaded into a computing device 24 from removable storage (e.g., a smart card, a flash drive, a removable disk, etc.) that enables the caregivers, patients, and/or other users to customize the implementation of computing devices 24. Other exemplary input devices and techniques adapted for use with computing devices 24 include, but are not limited to, an RS-232 port, an RF link, an IR link, a modem (telephone, cable, etc.), and/or other devices.

In some embodiments, all or some component of system 10 may communicatively be coupled via a network. The network may include the Internet and/or other networks, such as local area networks, cellular networks, Intranets, near field communication, frequency (RF) link, Bluetooth™, Wi-Fi™, and/or any type(s) of wired or wireless network(s). Such examples are not intended to be limiting, and the scope of this disclosure includes embodiments in which external resources 14, percussion excitation element(s) 16, sensor(s) 18, control unit(s) 20, electronic storage 22, and/or client computing device(s) 24 are operatively linked via some other communication media.

Figure 4:
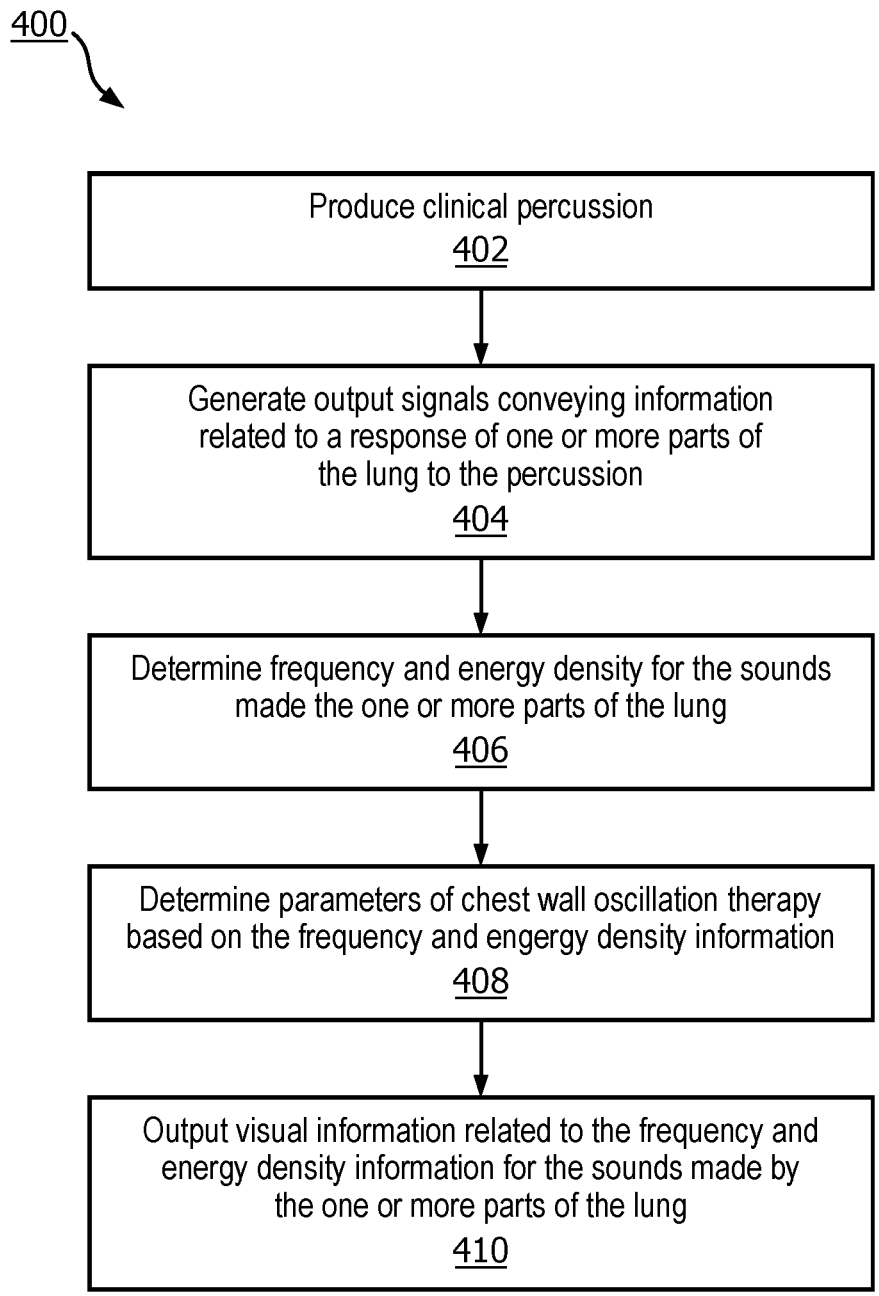
FIG. 4 illustrates example operations performed by a system configured to determine one or more parameters of chest wall oscillation therapy for a subject, in accordance with one or more embodiments.

FIG. 4 illustrates a method 400 for determining one or more parameters of chest wall oscillation therapy for a subject with a system. The system comprises a wearable garment, including one or more percussion excitation elements, and one or more sensors. The system further comprises a control unit, and/or other components. The control unit comprises one or more processors configured to execute one or more computer program components. The one or more computer program components may comprise a control component 30, a response component 32, a determination component 34, and/or other components. The operations of method 400 presented below are intended to be illustrative. In some embodiments, method 400 may be accomplished with one or more additional operations not described, and/or without one or more of the operations discussed. Additionally, the order in which the operations of method 400 are illustrated in FIG. 4 and described below is not intended to be limiting.

In some embodiments, method 400 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 400 in response to instructions stored electronically on an electronic storage medium. The one or more processing devices may include one or more devices configured through hardware, firmware, and/or software to be specifically designed for execution of one or more of the operations of method 400.

At an operation 402, percussion is produced. In some embodiments, percussion comprises mechanical pulsation of a chest wall of the subject in proximity to one or more parts of the lung. In some embodiments, operation 402 is performed by one or more percussion excitation elements the same as or similar to percussion excitation elements (s) 16 (shown in FIG. 1 and described herein).

At an operation 404, output signals conveying information related to a response of the one or more parts of the lung of the subject to the percussion are generated. In some embodiments, the response comprises sounds made by one or more parts of the lungs caused by the percussion. In some embodiments, operation 404 is performed by one or more sensors the same as or similar to sensor(s) 18 (shown in FIG. 1 and described herein).

At an operation 406, frequency and energy density information for the sounds made by the one or more parts of the lungs caused by the percussion may be determined. In some embodiments, the frequency and energy density information may be determined based on the output signals. In some embodiments, operation 406 is performed by a control unit the same as or similar to control unit 20 (shown in FIG. 1 and described herein).

At an operation 408, one or more parameters of the chest wall oscillation therapy may be determines. In some embodiments, the one or more parameters may be determined based on the frequency and energy density information. In some embodiments, operation 408 is performed by a control unit the same as or similar to control unit 20 (shown in FIG. 1 and described herein).

At an operation 410, visual information related to the frequency and energy density information for the sounds made by the one or more parts of the lungs may be output for display. In some embodiments, operation 410 is performed by a control unit the same as or similar to control unit 20 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system for chest wall oscillation therapy for a subject, the system comprising:
   (a) a wearable garment configured to provide percussion to one or more parts of a lung of the subject, the wearable garment comprising:
      (1) one or more percussion excitation elements configured to produce the percussion comprising mechanical pulsation of a chest wall of the subject resulting in a sound response to the percussion by the one or more parts of the lung, and
      (2) one or more sensors configured to generate output signals conveying resonant frequency information related to the sound response of the one or more parts of the lung of the subject to the percussion; and
   (b) a control unit operatively coupled to the one or more percussion excitation elements and the one or more sensors configured to:

(1) cause the one or more percussion excitation elements to produce the mechanical pulsation,
(2) determine one or more sound parameters comprising a peak resonant frequency for the sound response made by the one or more parts of the lungs caused by the percussion, and
(3) adjust, using the one or more sound parameters, a frequency value for a percussion excitation element of the one or more percussion excitation elements based on the peak resonant frequency of a part of the lung associated with the percussion excitation element;
wherein the frequency value for the percussion excitation element comprises a harmonic frequency setting lower than the peak resonant frequency, selected to achieve a harmonics frequency response for the part of the lung.

2. The system of claim 1, wherein the one or more sensors comprise one or more micro-electrical-mechanical system (MEMS) microphones configured to detect the sound response made by the one or more parts of the lungs caused by the percussion.

3. The system of claim 1, wherein the control unit is configured to use a frequency and an intensity value of the sound response to determine the peak resonant frequency.

4. The system of claim 1, wherein the control unit is configured to provide one or more of: visual information related to the sound response made by the one or more parts of the lungs for display and audio related to the sound response, and a control output that controls the one or more percussion excitation elements based on the one or more sound parameters.

5. The system of claim 1, wherein the one or more percussive excitation elements comprise two or more percussive excitation elements situated in the wearable garment to provide percussion to two or more parts of the lung,
the one or more sound parameters comprising two or more sound parameters, each identifying a different frequency value for a respective percussion excitation element based on resonant frequency information related to a respective sound response of a respective part of the lung.

6. The system of claim 1, wherein the harmonic frequency setting is between 5 Hz and 25 Hz.

7. The system of claim 1, wherein the control unit is configured to filter one or more heart beats from the output signals.

8. A method for chest wall oscillation therapy, the method comprising:
producing, with one or more percussion excitation elements of a wearable garment, percussion comprising mechanical pulsation of a chest wall of a subject resulting in a sound response to the percussion by one or more parts of a lung of the subject;
generating, with one or more sensors, output signals conveying resonant frequency information related to the sound response of the one or more parts of the lung of the subject to the percussion;
determining, with a control unit, one or more sound parameters comprising a peak resonant frequency for the sound response made by the one or more parts of the lung caused by the percussion; and
adjusting, using the one or more sound parameters a frequency value for a percussion excitation element of the one or more percussion excitation elements based on the peak resonant frequency of a part of the lung associated with the percussion excitation element;
wherein the frequency value for the percussion excitation element comprises a harmonic frequency setting lower than the peak resonant frequency, selected to achieve a harmonics frequency response for the part of the lung.

9. The method of claim 8, wherein the one or more sensors comprise one or more micro-electrical-mechanical system (MEMS) microphones configured to detect the sound response made by the one or more parts of the lung caused by the percussion.

10. The method of claim 8, further comprising outputting one or more of: visual information related to the sound response made by the one or more parts of the lung for display and audio related to the sound response.

11. The method of claim 8, wherein the adjusting comprises producing, with two or more percussion excitation elements of the wearable garment, percussion for two or more parts of the lung, each of the two or more percussion excitation elements being tuned to a different frequency value based on resonant frequency information related to a respective sound response of a respective part of the lung.

12. The method of claim 8, wherein the harmonic frequency setting is between 5 Hz and 25 Hz.

13. The method of claim 8, wherein the control unit is configured to filter one or more heart beats from the output signals.

14. The method of claim 8, wherein the adjusting comprises producing, with two or more percussion excitation elements of the wearable garment, percussion for two or more parts of the lung, each of the two or more percussion excitation elements being tuned to a different harmonic frequency based on peak resonant frequency information related to a respective sound response of a respective part of the lung.

15. A system for chest wall oscillation therapy for a subject, the system comprising:
(a) means for providing percussion to one or more parts of a lung of the subject, the means for providing percussion comprising:
(1) means for producing the percussion, the percussion comprising mechanical pulsation of a chest wall of the subject resulting in a sound response by the one or more parts of the lung, and
(2) means for generating output signals conveying resonant frequency information related to a sound response of the one or more parts of the lung of the subject to the percussion;
(b) means for determining one or more sound parameters comprising a peak resonant frequency for the sound response made by the one or more parts of the lung caused by the percussion; and
(c) means for adjusting, using the one or more sound parameters, a frequency value for one of the one or more means for percussion, based on the peak resonant frequency of a part of the lung associated with the one of the one or more means for percussion;
wherein the frequency value for the one of the one or more means for percussion comprises a harmonic frequency lower than the peak resonant frequency, setting selected to achieve a harmonics frequency response for the part of the lung.

16. The system of claim 15, wherein the means for generating output signals comprise one or more micro-electrical-mechanical system (MEMS) microphones configured to detect the sound response made by the one or more parts of the lung caused by the percussion.

17. The system of claim 15, comprising one or more of a means for outputting visual information related to the sound response made by the one or more parts of the lung for display and a means for outputting audio related to the sound response.

18. The system of claim 15, wherein the means for providing percussion comprises two or more percussive means situated in the wearable garment to provide percussion to two or more parts of the lung, the one or more sound parameters comprising two or more sound parameters, each identifying a different frequency value setting for a respective percussion means based on resonant frequency information related to a respective sound response of a respective part of the lung.

19. The system of claim 15, wherein the harmonic frequency setting is between 5 Hz and 25 Hz.

20. The system of claim 15, wherein the means for determining is configured to filter one or more heart beats from the output signals.

* * * * *